United States Patent [19]

Materne

[11] 4,380,547

[45] Apr. 19, 1983

[54] DIHYDROPYRIDINE COMPOUNDS WHICH ARE SUBSTITUTED IN THE 4-POSITION BY IMIDAZOLYL OR THIAZOLYL AND THEIR MEDICINAL USE

[75] Inventor: Carsten Materne, Bonn, Fed. Rep. of Germany

[73] Assignee: Bayer Aktiengesellschaft, Leverkusen, Fed. Rep. of Germany

[21] Appl. No.: 268,416

[22] Filed: May 29, 1981

[30] Foreign Application Priority Data

Jun. 12, 1980 [DE] Fed. Rep. of Germany ....... 3022030

[51] Int. Cl.³ .................. A61K 31/425; C07D 417/00
[52] U.S. Cl. .............................. 424/270; 424/273 N; 544/58.6; 544/105; 544/124; 544/235; 544/237; 544/284; 546/269; 546/270; 546/271; 546/275; 546/278; 546/279; 546/280
[58] Field of Search ...................... 544/405, 58.6, 124; 546/275, 277, 278, 279, 280; 424/250, 246, 248.55, 263

[56] References Cited

U.S. PATENT DOCUMENTS 3,511,837  5/1970  Bossert et al. ....................... 544/333
3,773,773  11/1973  Bossert ................................. 546/257
4,145,432  5/1979  Sato ..................................... 546/280

OTHER PUBLICATIONS

Neumann, Chem. Ab., vol. 93, (1980), 239419.

*Primary Examiner*—Henry R. Jiles
*Assistant Examiner*—Bernard Dentz
*Attorney, Agent, or Firm*—Sprung, Horn, Kramer & Woods

[57] ABSTRACT

The invention relates to dihydropyridine compounds of formula (I) as defined in the specification, containing a hetero-ring substituent in the 4-position. Also included in the invention are pharmaceutical compositions containing said compounds of formula (I) and methods for the use of said compounds and compositions. The said compounds are useful for influencing circulation.

11 Claims, No Drawings

DIHYDROPYRIDINE COMPOUNDS WHICH ARE SUBSTITUTED IN THE 4-POSITION BY IMIDAZOLYL OR THIAZOLYL AND THEIR MEDICINAL USE

The present invention relates to certain new dihydropyridine compounds which are substituted in the 4-position by a hetero-ring, to several processes for their production and to their use as medicaments, medicaments which have an influence on the circulation, in particular as hypotensive medicaments and medicaments having a coronary action.

It is already known that 1,4-dihydropyridine derivatives have circulation-influencing properties. Thus, for example, 2,6-dimethyl-4-(2'-nitrophenyl)-1,4-dihydropyridine-3,5-dicarboxylic acid dimethyl ester, a compound known under the Trade Mark "Nifedipin", (see German Patent Specification No. 1,607,827) is known as a compound which has a vasodilative action on the coronary vessels.

According to the present invention there are provided compounds which are 1,4-dihydropyridines of the formula

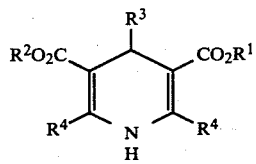

or a salt thereof, diastereomer mixtures thereof or racemic forms and antipodes thereof, in which $R^3$ represents a heterocyclic radical selected from pyrazolyl, imidazolyl, oxazolyl, isoxazolyl, thiazolyl, isothiazolyl, triazolyl, oxadiazolyl, thiadiazolyl, pyrazinyl, oxazinyl, thiazinyl, indolizinyl, indolyl, benzofuranyl, benzothienyl, indazolyl, benzimidazolyl, benzoxazolyl, benzisoxazolyl, benzothiazolyl, benzisothiazolyl, benzotriazolyl, benzoadiazolyl, benzothiadiazolyl, cinnolinyl, quinoxazinyl, quinazolinyl, phthalazinyl, naphthyridinyl and benzotriazinyl, the heterocyclic radical optionally containing 1, 2 or 3 identical or different substituents selected from phenyl, alkyl, alkoxy, alkylene, dioxyalkylene, halogen, trifluoromethyl, trifluoromethoxy, amino, alkylamino, nitro, cyano, azido, carboxamido, sulfonamido and $SO_m$-alkyl (in which m is 0 or 2), $R^4$ represents, in both instances, a hydrogen atom, a straight-chain or branched alkyl radical, an aryl radical or an aralkyl radical and $R^1$ and $R^2$ are identical or different and each represent a straight-chain, branched or cyclic, saturated or unsaturated hydrocarbon radical, which is optionally interrupted in the chain by one oxygen atom and/or which is optionally substituted by halogen, pyridyl, phenyl or phenoxy (it being possible for the phenyl substituent or phenyl part of the phenoxy substituent in turn to be substituted by halogen, cyano, dialkylamino, alkoxy, alkyl, trifluoromethyl or nitro), or the hydrocarbon radical is optionally substituted by an amino group, this amino group being substituted by two identical or different substituents selected from alkyl, alkoxyalkyl, aryl and aralkyl, or this amino group being substituted such that the 2 substituents, together with the nitrogen atom, form a 5-membered to 7-membered ring, which can contain, as a further hetero-atom, oxygen, sulphur or a N-alkyl grouping.

As used herein and unless otherwise specified the terms "alkyl" and "alkoxy" preferably contain 1 to 8, especially 1 to 4 carbon atoms; the term "alkylene" preferably contains 2 to 6 carbon atoms; the term "dioxyalkylene" preferably contains 1 to 4 carbon atoms; the term "halogen" is preferably chlorine, bromine or fluorine; the term "alkylamino" and "dialkylamino" preferably contain 1 to 8, especially 1 to 4 carbon atoms in each alkyl group; the term "aryl" is preferably mono- or bi-cyclic carbocyclic aryl; the term "aralkyl" is preferably mono- or bi-cyclic carbocyclic aryl in the "ar" position and contains 1 to 4, especially 1 or 2 carbon atoms in the alkyl portion.

1,4-Dihydropyridines which are substituted by the described and claimed heterocyclic radicals have not previously been described.

The racemic forms, like the diastereomers, can be separated into stereoisomerically pure constituents by known methods (see, for example, B. E. Eliel, Stereochemistry of Carbon Compounds, McGraw Hill, 1962).

Racemate mixtures can be separated into the pure racemates in a known manner on the basis of the physicochemical differences of the constituents, for example by chromatography and/or fractional crystallization.

Pure racemates can be resolved according to known methods, for example by recrystallization from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

The compound of the present invention have circulation-influencing properties, and in particular they dilate the coronary vessels and lower the blood pressure.

Preferred compounds of the present invention are those in which $R^3$ represents a heterocyclic radical selected from pyrazolyl, imidazolyl, oxazolyl, isoxazolyl, thiazolyl, triazolyl, oxadiazolyl, pyrazinyl, oxazinyl, thiazinyl, indolizinyl, indolyl, benzofuranyl, indazolyl, benzothienyl, benzimidazolyl, benzoxazolyl, benzisoxazolyl, benzothiazolyl, benzotriazolyl, benzoxadiazolyl, cinnolinyl, phthalazinyl, naphthyridinyl and benzotriazinyl the heterocyclic radical optionally containing 1, 2 or 3 identical or different substituents selected from phenyl, alkyl with 1 to 4 carbon atoms, alkoxy with 1 to 4 carbon atoms, alkylene with 3 to 5 carbon atoms, dioxyalkylene with 1 to 3 carbon atoms, fluorine, chlorine, bromine, trifluoromethyl, trifluoromethoxy, alkylamino or dialkylamino with in each case 1 or 2 alkyl groups, which each contain 1 to 4 carbon atoms, nitro, cyano, azido, carboxamide, sulfonamido, amino and $SO_m$-alkyl (in which m is 0 or 2 and "alkyl" contains 1 to 4 carbon atoms), R⁴ represents, in both instances, a hydrogen atom, a straight-chain or branched alkyl radical with 1 to 4 carbon atoms, a phenyl radical or a benzyl radical and R¹ and R² are identical or different and each represents a straight-chain, branched or cyclic saturated or unsaturated hyrocarbon radical which has up to 8 carbon atoms and is optionally interrupted in the chain by an oxygen atom and/or is optionally substituted by fluorine, chlorine, pyridyl, phenyl or phenoxy (it being possible for the phenyl substituent or phenyl part of the phenoxy substituent in turn to be substituted by fluorine, chlorine, bromine, cyano, trifluoromethyl, nitro, dialkylamino with 1 to 4 carbon atoms per alkyl radical, alkoxy with 1 to 4 carbon atoms or alkyl with 1 to 4 carbon atoms), or the hydrocarbon radical is optionally substituted by an amino group, which is in turn substituted by 2 identical or different substituents selected from alkyl with 1 to 4 carbon atoms, alkoxyalkyl with 2 to 6 carbon atoms, phenyl, benzyl or phenethyl, or the amino group being substituted such that the two substituents, together with the nitrogen atom, form a 5-membered to 7-membered ring, which can contain, as a further hetero-atom, oxygen, or a N-methyl grouping.

Particularly preferred compounds of the present invention are those in which

R³ represents a 5-membered heterocyclic radical of the imidazole or thiazole series which is optionally substituted by alkyl with 1 to 4 carbon atoms or phenyl, R⁴ represents, in both instances, a methyl, ethyl, phenyl or benzyl radical and R¹ and R² are identical or different and represent a straight-chain or branched saturated or unsaturated hydrocarbon radical which has up to 6 carbon atoms and is optionally interrupted in the chain by an oxygen atom and/or is optionally substituted by fluorine or chlorine.

According to the present invention there is further provided a process for the production of a compound of the present invention in which (a) an aldehyde of the formula (II)

in which R³ has the above-mentioned meaning, is reacted with ammonia and with an acetoacetic acid ester of the formula

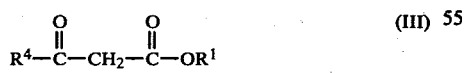

in which R¹ and R² have the above-mentioned meaning, or with an enamino-ester of the formula

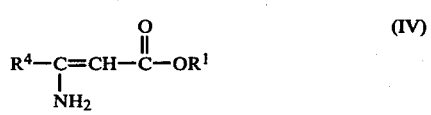

in which R¹ and R⁴ have the above-mentioned meaning, in an organic solvent, a compound of the present invention with symmetric ester groups (R¹=R²) being obtained by this process variant, or (b) an ylidene compound of the formula

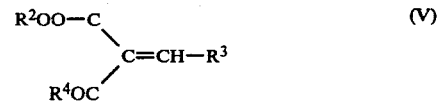

in which R², R³ and R⁴ have the above-mentioned meaning, is reacted with an enamino-ester of the formula (IV), as defined above, in an organic inert solvent.

The organic solvent can be an alcohol, (such as methanol, ethanol, isopropanol, etc), dioxane, ethyl acetate, glacial acetic acid, dimethylformamide or acetonitrile. The reaction temperatures generally are varied within a range between 20° and 150° C. The reaction is preferably carried out at the boiling point of the solvent.

The starting substances which can be used are in most cases known compounds, or they can be prepared by known processes.

Examples of aldehydes of the formula (II) which may be mentioned are: thiazole-2-aldehyde, 2-phenyl-thiazole-4-aldehyde, 2-methylthiazole-4-aldehyde and 1-methylimidazole-2-aldehyde.

Suitable acetoacetic acid esters of formula (III) for this reaction are, for example: methyl acetoacetate, ethyl acetoacetate, propyl acetoacetate, isopropyl acetoacetate, n-butyl acetoacetate, sec.-butyl acetoacetate and isobutyl acetoacetate.

The enamino-esters of the formula (IV) which are suitable for the reaction are obtained from the corresponding acetoacetates of the formula (III) by reaction with ammonia.

As stated above, the invention also relates to the use in medicine of the compounds of the invention.

The present invention provides pharmaceutical compositions containing, as active ingredient a compound of the invention in admixture with an inert pharmaceutical carrier, e.g. a solid or liquified gaseous diluent, or in admixture with a liquid diluent other than a solvent of a molecular weight less than 200 (preferably less than 350) except in the presence of a surface active agent.

The invention further provides pharmaceutical compositions containing, as active ingredient, a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, aliginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 2.5 to 250 mg of active ingredient, and for oral administration is 2.5 to 250 mg of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously) or rectally, preferably orally or parenterally, especially perlingually or intravenously. Preferred pharmaceutical compositions and medicaments are therefore those adapted for administration such as oral or parenteral administration. Administration in the method of the invention is preferably oral or parenteral administration.

In general it has proved advantageous to administer intravenously amounts of from 0.01 mg to 10 mg/kg, preferably 0.05 to 5 mg/kg, of body weight per day and to administer orally amounts of from 0.05 mg to 20 mg/kg, preferably 0.5 mg to 5 mg/kg, of body weight per day, to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The processes according to the present invention for the production of compounds of the invention are illustrated by the following Examples.

EXAMPLE 1

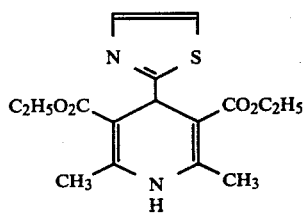

(a)
2,6-Dimethyl-4-thiazol-2-yl-1,4-dihydropyridine-3,5-dicarboxylic acid diethyl ester 18 g of 2-formylthiazole together with 41.5 g of ethyl acetoacetate and 12 ml of ammonia (33% strength) in 100 cm$^3$ of ethanol were heated under reflux for 4 to 5 hours. The mixture was concentrated, the residue was allowed to cool and the precipitate was recrystallised from ethanol.

Yield: 20 g (40%);
melting point: 184° C. to 186° C.

The following compounds were obtained in an analogous manner: (b) 2,6-dimethyl-4-thiazol-2-yl-1,4-dihydropyridine-3,5-dicarboxylic acid dimethyl ester, (c) 2,6-dimethyl-4-thiazol-2-yl-1,4-dihydropyridine-3,5-dicarboxylic acid diisopropyl ester, (d) 2,6-dimethyl-4-thiazol-2-yl-1,4-dihydropyridine-3,5-dicarboxylic acid dibutyl ester, (e) 2,6-dimethyl-4-thiazol-2-yl-1,4-dihydropyridine-3,5-dicarboxylic acid dipropyl ester and (f) 2,6-dimethyl-4-thiazol-2-yl-1,4-dihydropyridine-3,5-dicarboxylic acid diisobutyl ester.

EXAMPLE 2

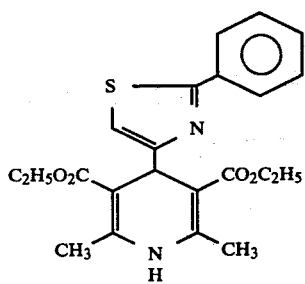

(a)
2,6-Dimethyl-4-(2'-phenylthiazol-4-yl)-1,4-dihydropyridine-3,5-dicarboxylic acid diethyl ester 18.9 g of 2-phenyl-4-formylthiazole and 25.8 g of ethyl β-aminocrotonate in 100 cm$^3$ of ethanol were heated under reflux for 8 hours. The mixture was concentrated and the residue was allowed to cool and was recrystallised from ethanol.

Yield: 28.8 g (70%);
melting point: 160° C.

The following compounds were obtained in an analogous manner: (b) 2,6-dimethyl-4-(2'-phenylthiazol-4-yl)-1,4-dihydropyridine-3,5-dicarboxylic acid dimethyl ester, (c) 2,6-dimethyl-4-(2'-phenylthiazol-4-yl)-1,4-dihydropyridine-3,5-dicarboxylic acid diisopropyl ester and (d) 2,6-dimethyl-4-(2'-phenylthiazol-4-yl)-1,4-dihydropyridine-3,5-dicarboxylic acid dibutyl ester.

EXAMPLE 3

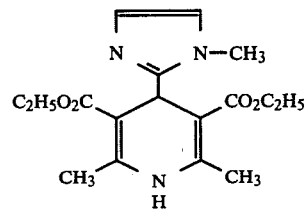

(a)
2,6-Dimethyl-4-(1-methylimidazol-2-yl)-1,4-dihydropyridine-3,5-dicarboxylic acid diethyl ester 11 g of 1-methyl-2-formylimidazole and 25.8 g of ethyl β-aminocrotonate in 100 cm$^3$ of ethanol were heated under reflux for 4 hours. After cooling the mixture, the precipitate was filtered off and recrystallised from ethanol.

Yield: 10 g (30%);
melting point: 223° to 227° C.

The following compound was obtained in an analogous manner: (b) 2,6-dimethyl-4-(1-methylimidazol-2-yl)-1,4-dihydropyridine-3,5-dicarboxylic acid methyl ester.

EXAMPLE 4

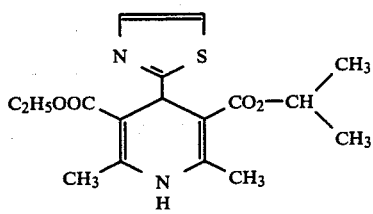

(a)
2,6-Dimethyl-4-thiazol-2-yl-1,4-dihydropyridine-3,5-dicarboxylic acid 3-ethyl 5-isopropyl ester 24.1 g of α-acetyl-β-2-thiazolylacrylic acid ethyl ester and 14.3 g of isopropyl β-aminocrotonate in 100 cm$^3$ of ethanol were heated under reflux for 3 hours. After cooling the mixture, the product crystallised out. For purification, the product was recrystallised from ethanol.

Yield: 14 g (40%);
melting point: 165° to 168° C.

The following compounds were obtained in an analogous manner: (b) 2,6-dimethyl-4-thiazol-2-yl-1,4-dihydropyridine-3,5-dicarboxylic acid 3-ethyl 5-methyl ester and (c) 2,6-dimethyl-4-thiazol-2-yl-1,4-dihydropyridine-3,5-dicarboxylic acid 3-ethyl 5-propyl ester.

Among the new 1,4-dihydropyridine salts of the invention, those salts that are pharmaceutically acceptable (acid-addition salts) are particularly important and are preferred.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The new free 1,4-diydropyridines of the general formula (I) and their salts can be interconverted in any suitable manner; methods for such interconversion are known in the art.

The present invention also comprises pharmaceutically acceptable bioprecursors of the active compounds of the present invention.

For the purposes of this specification the term "pharmaceutically acceptable bioprecursor" of an active compound of the invention means a compound having a structural formula different from the active compound but which nonetheless, upon administration to an animal or is convered in the patient's body to the active compound.

What is claimed is:

1. A compound which is a 1,4-dihydropyridine of the formula

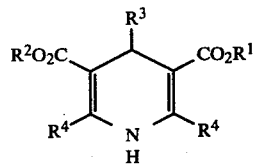

in which
   $R^3$ represents imidazolyl or thiazolyl which is optionally substituted by alkyl with 1 to 4 carbon atoms or phenyl
   $R^4$ represents in both instances methyl, ethyl, phenyl or benzyl,
   $R^1$ and $R^2$ are identical or different and represent a straight-chain or branched saturated hydrocarbon radical which has up to 6 carbon atoms and is optionally interrupted in their chain by an oxygen atom and/or is optionally substituted by fluorine or chlorine.

2. A compound according to claim 1, in which $R^3$ represents imidazolyl or thiazolyl which is optionally substituted by alkyl with 1 to 4 carbon atoms or phenyl, $R^4$ represents, in both instances, a methyl group, and $R^1$ and $R^2$ are identical or different and each represent a straight-chain or branched alkyl radical with 1 to 4 carbon atoms.

3. A compound according to claim 1 which is 2,6-dimethyl-4-thiazol-2-yl-1,4-dihydropyridine-3,5-dicarboxylic acid diethyl ester.

4. A pharmaceutical composition containing as an active ingredient an amount effective of vasodilating, of a compound according to claim 1 in admixture with an inert pharmaceutical carrier.

5. A pharmaceutical composition of claim 4 in the form of a sterile or physiologically isotonic aqueous solution.

6. A composition according to claim 4 or 5, containing from 0.5 to 90% by weight of the said active ingredient.

7. A medicament in dosage unit form comprising an amount effective for vasodilating, of a compound according to claim 1.

8. A medicament of claim 7 in the form of tablets, pills, dragees, capsules, ampoules, or suppositories.

9. A method of combating circulatory illnesses in warm-blooded animals which comprises administering to the animals an amount effective for vasodilating, of a compound according to claim 1 either alone or in admixture with an inert pharmaceutical carrier or in the form of a medicament.

10. A method according to claim 9 in which the active compound is administered intravenously in an amount of 0.01 to 10 mg per kg body weight per day.

11. A method according to claim 9 in which the active compound is administered orally in an amount of 0.05 to 20 mg per kg body weight per day.

* * * * *